(12) United States Patent
Heng et al.

(10) Patent No.: US 8,639,012 B2
(45) Date of Patent: Jan. 28, 2014

(54) SERIAL-LINE-SCAN-ENCODED MULTI-COLOR FLUORESCENCE MICROSCOPY AND IMAGING FLOW CYTOMETRY

(75) Inventors: Xin Heng, Hercules, CA (US); Paul Patt, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 767 days.

(21) Appl. No.: 12/726,628

(22) Filed: Mar. 18, 2010

(65) Prior Publication Data

US 2010/0238442 A1  Sep. 23, 2010

Related U.S. Application Data

(60) Provisional application No. 61/232,113, filed on Aug. 7, 2009, provisional application No. 61/162,072, filed on Mar. 20, 2009.

(51) Int. Cl.
 *G06K 9/00* (2006.01)
(52) U.S. Cl.
 USPC ............................................. 382/133
(58) Field of Classification Search
 USPC ............................................. 382/133
 See application file for complete search history.

(56) References Cited

U.S. PATENT DOCUMENTS

| | | | | |
|---|---|---|---|---|
| 4,920,275 | A * | 4/1990 | Itoh | 250/574 |
| 5,426,499 | A * | 6/1995 | Kosaka et al. | 356/39 |
| 5,437,946 | A | 8/1995 | McCoy | |
| 5,448,349 | A * | 9/1995 | Kosaka | 356/73 |
| 5,475,487 | A | 12/1995 | Mariella, Jr. et al. | |
| 5,480,775 | A * | 1/1996 | Ito et al. | 435/7.2 |
| 5,721,433 | A * | 2/1998 | Kosaka | 250/573 |
| 6,243,189 | B1 | 6/2001 | Ribes et al. | |
| 6,275,777 | B1 | 8/2001 | Shimizu | |
| 6,713,019 | B2 * | 3/2004 | Ozasa et al. | 422/82.09 |
| 7,385,682 | B2 * | 6/2008 | Chu et al. | 356/73 |
| 7,518,723 | B2 * | 4/2009 | Adams et al. | 356/338 |

(Continued)

FOREIGN PATENT DOCUMENTS

EP  1474033 B1  9/2008

OTHER PUBLICATIONS

International Search Report and Written Opinion of PCT/US2012/025969 mailed on Apr. 17, 2012, 11 pages.

(Continued)

*Primary Examiner* — Roy M Punnoose
(74) *Attorney, Agent, or Firm* — Kilpatrick Townsend & Stockton LLP

(57) ABSTRACT

A system for performing high-speed, high-resolution imaging cytometry utilizes a line-scan sensor. A cell to be characterized is transported past a scan region. An optical system focuses an image of a portion of the scan region onto at least one linear light sensor, and repeated readings of light falling on the sensor are taken while a cell is transported though the scan region. The system may image cells directly, or may excite fluorescence in the cells and image the resulting light emitted from the cell by fluorescence. The system may provide a narrow band of illumination at the scan region. The system may include various filters and imaging optics that enable simultaneous multicolor fluorescence imaging cytometry. Multiple linear sensors may be provided, and images gathered by the individual sensors may be combined to construct an image having improved signal-to-noise characteristics.

26 Claims, 8 Drawing Sheets

(56) References Cited

U.S. PATENT DOCUMENTS

| | | | |
|---|---|---|---|
| 7,551,279 B2 * | 6/2009 | Adams et al. | 356/338 |
| 7,561,267 B2 * | 7/2009 | Luo et al. | 356/336 |
| 7,605,919 B2 * | 10/2009 | Oma et al. | 356/339 |
| 7,616,311 B2 * | 11/2009 | Adams et al. | 356/338 |
| 7,634,126 B2 * | 12/2009 | Ortyn et al. | 382/133 |
| 7,800,742 B2 * | 9/2010 | Fukuda et al. | 356/73 |
| 7,852,538 B2 | 12/2010 | Kanesaka et al. | |
| 8,018,592 B2 * | 9/2011 | Tabata | 356/338 |
| 8,131,053 B2 * | 3/2012 | Ortyn et al. | 382/133 |
| 2006/0221325 A1 | 10/2006 | Wells | |
| 2008/0174842 A1 | 7/2008 | Cromwell et al. | |
| 2010/0238442 A1 | 9/2010 | Heng et al. | |
| 2011/0017915 A1 | 1/2011 | Curry | |

OTHER PUBLICATIONS

International Preliminary Report on Patentability of PCT/US2010/027843 mailed on Sep. 29, 2011, 7 pages.

International Search Report and Written Opinion for PCT application No. PCT/US2010/027843, mailed Jul. 21, 2010.

* cited by examiner

SERIAL-LINE-SCAN-ENCODED MULTI-COLOR FLUORESCENCE MICROSCOPY AND IMAGING FLOW CYTOMETRY

This application claims priority to U.S. Provisional Patent Application No. 61/162,072, filed Mar. 20, 2009, and U.S. Provisional Patent Application No. 61/232,113, filed Aug. 7, 2009, the disclosures of which are incorporated herein by reference for all purposes.

BACKGROUND OF THE INVENTION

Cytometry is a technical specialty concerned with the counting and characterization of biological cells. FIG. 1 shows a simplified diagram of one technique known as flow cytometry. In a basic form of flow cytometry, cells 101 are suspended in a fluid and entrained single-file in a narrow transparent tube 102. The entrainment can be accomplished by any of several methods, including hydrodynamic focusing. A light source 103 illuminates each cell 101 as it passes a measurement location 104. Light source 103 may be, for example, a laser. Light from light source 103 is scattered by the cell 101 being measured. Some light 105 is scattered generally in the same direction as it traveled to reach the cell 101. Light 105 is sometimes called "forward scatter", and may be collected by a forward sensor 106. Some light may be scattered in other directions as well. This light may be called "side scatter", and some of the side scattered light 107 may be collected by one or more other sensors 108. Output signals from sensors 106 and 108 are sent to a computer 109, which may store and analyze the signals. By analyzing the amount and distribution of the scattered light, it is possible to discern information about each cell, for example its size and some information about its internal structure.

Flow cytometry may measure the scattered light directly, or may make use of fluorescence. In fluorescence cytometry, the cells may be marked with one or more fluorophores, which are excited by light from source 103 to produce light by fluorescence. The nature of the emitted light may reveal additional information about the cells.

The technique shown in FIG. 1 relies entirely on measurements of scattered light to infer information about the cell structure, but does not produce an image of any particular cell. In another technique, called "image cytometry", an image of an individual cell may be recorded by a camera or microscope.

BRIEF SUMMARY OF THE INVENTION

An improved image cytometry system performs high-speed, high-resolution cytometry using a linear light sensor. In some embodiments, light from a light source is concentrated onto an oblong scanning region, illuminating a cell that is being transported through the scanning region. An optical system focuses an image of a portion of the scanning region onto a linear light sensor. The system repeatedly takes readings of light falling on the linear sensor. The system may include a slit aperture proximate the linear light sensor, such that the system performs semi-confocal imaging.

In some embodiments, light from a light source illuminates a cell that is being transported through the scanning region. An optical system focuses an image of a portion of the scanning region onto at least two parallel linear light sensors. The system repeatedly takes readings of light falling on the linear light sensors. The system may include a slit aperture proximate the linear light sensor, such that the system performs semi-confocal imaging. In some embodiments, images gathered by the individual linear light sensors are combined to form an image with improved signal-to-noise characteristics as compared with an image gathered by a single linear light sensor. The combination may be performed by digitally combining pixel values from the respective images corresponding to substantially the same respective locations on the cell. The combination may be performed by time delay integration. In some embodiments, light from the light source is concentrated onto an oblong field at the scanning region.

In another embodiment, a system for performing cytometry comprises a scanning region that is illuminated by light including at least first and second wavelength bands, and means for transporting a cell through the scanning region such that the cell is illuminated. The system further comprises first and second sets of linear light sensors, each set comprising at least one linear light sensor, and an optical system. The optical system selectively directs light emitted from the cell to the two linear light sensor sets such that emitted light in a third wavelength band is primarily directed to the first linear light sensor set, and emitted light in a fourth wavelength band is primarily directed to the second linear light sensor set. The system repeatedly takes readings of light falling on the linear sensors while the cell is transported through the scanning region. Each light sensor set may comprise at least two linear light sensors. The emitted light may be emitted as a result of fluorescence. The system may include an objective lens that receives and redirects light emitted from the cell, and a mirror that reflects a first portion of the redirected light to the first linear light sensor set and transmits a second portion of the redirected light. The system may comprise a first tube lens that receives the first portion of light and cooperates with the objective lens to form an image of the cell on the first linear light sensor set. In some embodiments, the system may also comprise a second tube lens that receives the second portion of light and cooperates with the objective lens to form an image of the cell on the second linear light sensor set. The system may include a slit aperture proximate at least one of the sets of linear light sensors, such that the system performs semi-confocal imaging. In some embodiments, each set of linear light sensors comprises at least two linear light sensors, and for each set of linear light sensors, images gathered by the individual linear light sensors in the set are combined to form an image with improved signal-to-noise characteristics as compared with an image gathered by a single linear light sensor in the set. The combination may be performed by digitally combining pixel values from the respective images corresponding to substantially the same respective locations on the cell. The combination may be performed by time delay integration.

In another embodiment, a system for performing cytometry comprises a scanning region that is illuminated by light including at least first and second wavelength bands, and means for transporting a cell through the scanning region such that the cell is illuminated. The system further includes a set comprising at least one linear light sensor, and an optical system. The optical system selectively directs light emitted from the cell to two portions of the linear light sensor set such that emitted light in a third wavelength band is primarily directed to a first portion of the linear light sensor set, and emitted light in a fourth wavelength band is primarily directed to a second portion of the linear light sensor set. The system repeatedly takes readings of light falling on the linear light sensor set while the cell is transported through the scanning region. The set may comprise at least two linear light sensors. The emitted light may be emitted as a result of fluorescence. The system may include a slit aperture proximate the linear light sensor set, such that the system performs semi-confocal imaging. In some embodiments, the set comprises at least two linear light sensors, and images gathered by the individual linear light sensors in the set are combined to form an image with improved signal-to-noise characteristics as compared with an image gathered by a single linear light sensor in the set. The combination may be performed by digitally combining pixel values from the respective images corresponding to substantially the same respective locations on the cell. The combination may be performed by time delay integration.

In another embodiment a system for performing cytometry includes a scanning region that is illuminated by a light source, a set comprising at least one linear light sensor, and an optical system that focuses an image of a portion of the scanning region onto the linear light sensor set. The system repeatedly takes readings of light falling on the linear light sensor set while a cell is transported through the scanning region and illuminated by the light source. In this embodiment, the system is configurable such that during a first experiment, a first image is created having a first number of pixels in a dimension corresponding to the length of the linear light sensor set, and during a second experiment, a second image is created having a second number of pixels in the dimension corresponding the length of the linear light sensor set, the second number of pixels being fewer than the first. The set may comprise at least two linear light sensors. The number of pixels in the second image may be reduced by selecting fewer than all of the pixels from the linear light sensor set. The number of pixels the second image may be reduced by binning some or all of the pixels from the linear light sensor set. Each reading of light falling on a particular one of the linear sensors may result in a single numerical representation of the amount of light falling on the particular sensor.

In another embodiment, a system for producing an oblong illumination field includes a laser that produces a beam, a cylindrical lens that receives the beam and causes the beam to converge in only a first axis, and an objective lens that receives the beam after the cylindrical lens. The objective lens is part of an infinity-corrected optical system, and causes the beam to converge in a second axis orthogonal to the first. The system may include a wavelength-selective mirror between the cylindrical lens and the objective lens. In some embodiments, the objective lens is spaced from the cylindrical lens by a distance less than the focal length of the cylindrical lens. In some embodiments, the objective lens is spaced from the cylindrical lens by a distance greater than the focal length of the cylindrical lens. In some embodiments, the beam is diverging in the first axis as it leaves the objective lens. In some embodiments, the beam is converging in the first axis as it leaves the objective lens.

In another embodiment, a method of performing cytometry comprises illuminating, using a light source, an oblong field at a scanning region, wherein illuminating the oblong field further includes concentrating, using a light shaping element, light from the light source onto the oblong field. The method further comprises focusing, using an optical system, an image of a portion of the scanning region onto a linear light sensor, and repeatedly taking readings of light falling on the linear sensor while a cell is transported through he scanning region and illuminated by the light source. In some embodiments, the method further comprises passing the light falling on the linear light sensor through a slit aperture proximate the linear light sensor, such that the system performs semi-confocal imaging.

In another embodiment, a method of performing cytometry comprises illuminating a scanning region using a light source, and focusing, using an optical system, an image of a portion of the scanning region onto at least two parallel linear light sensors. The method of this embodiment further comprises repeatedly taking readings of light falling on the two parallel light sensors while a cell is transported through the scanning region and illuminated by the light source. In some embodiments, the method further comprises combining images gathered by the individual linear light sensors to form an image with improved signal-to-noise characteristics as compared with an image gathered by a single linear light sensor. Combining images may further include digitally combining pixel values from the respective images corresponding to substantially the same respective locations on the cell. Combining images may further include combining images using time delay integration. In some embodiments, the light source produces illumination including light in at least first and second wavelength bands, and the method further comprises directing, using the optical system, light emitted from the cell in a third wavelength band primarily to one of the two parallel light sensors, and directing, using the optical system, light emitted from the cell in a fourth wavelength band primarily to the other of the two parallel linear light sensors. In some embodiments, the method further comprises focusing, using the optical system, an image of a portion of the scanning region onto at least two sets of parallel linear light sensors, each set comprising at least two linear light sensors.

DETAILED DESCRIPTION OF THE INVENTION

Figure 1:
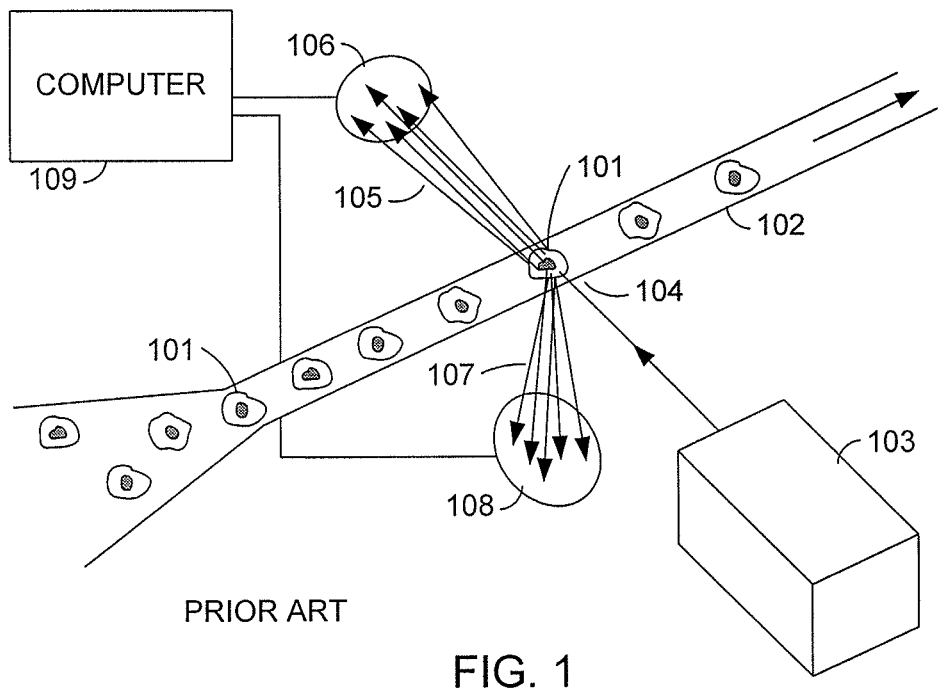
FIG. 1 shows a simplified diagram of a technique known as flow cytometry.
Figure 2:
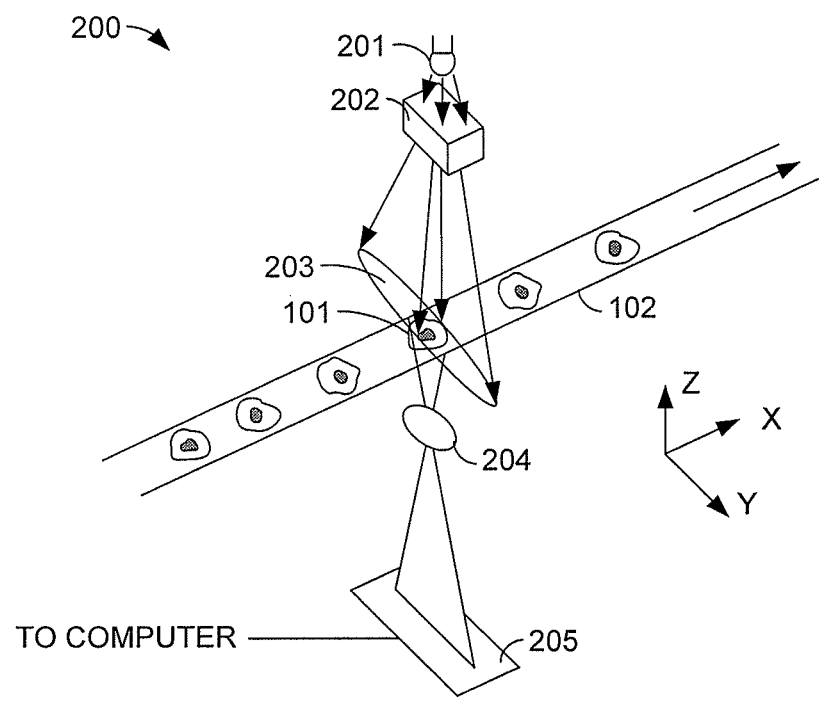
FIG. 2 shows a simplified conceptual diagram of a high-speed, high-resolution line scan image cytometry system in accordance with an embodiment.

FIG. 2 shows a simplified conceptual diagram of a high-speed, high-resolution line scan image cytometry system 200 in accordance with an embodiment. The system of FIG. 2 is a flow cytometry system, although one of skill in the art will recognize that embodiments of the invention may be utilized in other kinds of cytometry as well.

Cells 101 are entrained in fluid to progress through tube 102 in single file. The system may be used to characterize cells of many different kinds, but in a typical application, cells 101 may be, for example, about 10 to 20 micrometers across, and may progress through tube 102 at a speed of, for example, 10 millimeters per second. A light source 201 provides field of light 203 onto tube 102. Light source 201 may be a laser, a light-emitting diode, an incandescent light source, a fluorescent light source or another kind of light source. Light source 201 may produce substantially monochromatic light, broad spectrum light, or light containing two or more narrow bands of wavelengths. Optional light shaping element 202 may include various lenses, prisms, reflectors, or other optical components to concentrate light from light source 201 into oblong or slit-shaped field 203, through which cells 101 are transported. Because, as is described below, only a narrow line image will be scanned, only a narrow field need be illuminated, in contrast to traditional epi-illumination in which the entire objective field is illuminated. The concentration provided by light shaping element 202 can increase the effective illumination level by as much as two to six orders of magnitude as compared with normal, symmetric epi-illumination.

Some light from source 201 is transmitted through or scattered by one of cells 101, at least a portion of which is within field 203. Some of the light is redirected by one or more lenses 204 onto a linear sensor 205. Linear sensor 205 may be, for example a charge-coupled device (CCD) sensor, a complementary metal oxide semiconductor (CMOS) sensor, or another kind of sensor having a plurality of light-sensitive sites arranged in a row. Lens 204 and sensor 205 may be, for example parts of a line scan camera such as a Basler Sprint line scan CMOS camera available from Basler AG of Ahrensburg, Germany. The individual sensor sites are sometimes called "pixels". The corresponding sites at the scan line sensed by the sensor pixels are also sometimes called pixels. Sensor 205 may comprise, for example, one or more rows of pixels, each row containing 512, 1024, 2048, or another appropriate number of pixels. The intensity of light falling on the row of pixels may be read by clearing the pixel array, allowing charge to accumulate in the pixel sites for a predetermined exposure time, and then converting the accumulated charge amounts to numerical values representing the light intensities. This process is performed repeatedly as the cells pass the scan area. In one example embodiment, the system may take a reading ("scan a line") every 20 microseconds, or at a scan rate of 50 kHz. Using a cell transport speed of 10 millimeters per second and a scan rate of 50 kHz results in an imaging pixel size of 200 nm. Other transport speeds and scan rates are possible, and may result in other imaging pixel sizes. The resulting array of measurements can be reassembled into an approximate image of a cell.

Figure 3A:
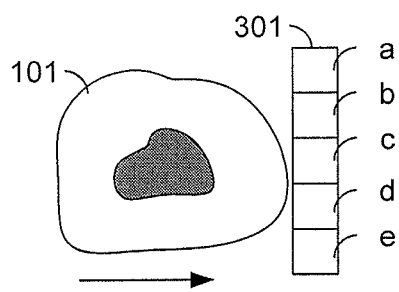
FIGS. 3A-3C illustrate an image forming process.
Figure 3B:
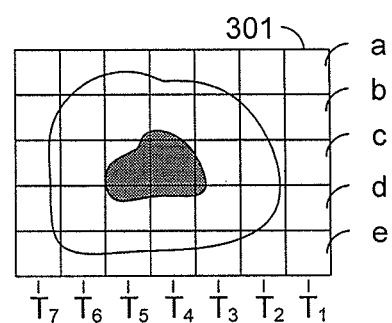
Figure 3C:
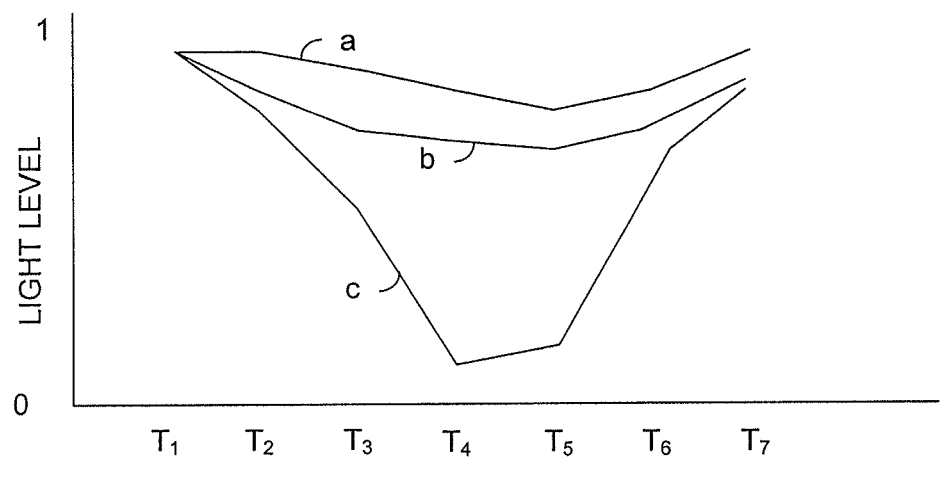
Figure 3D:
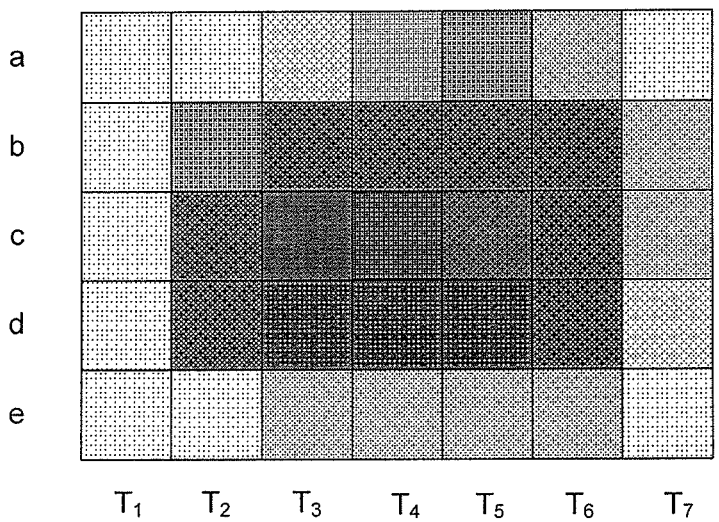
FIG. 3D illustrates an example reconstructed image.

FIGS. 3A-3C illustrate the image forming process. In FIG. 3A, a scan line 301 includes pixels a, b, c, d, and e. A cell 101 is transported past scan line 301, as shown in FIG. 3B, which shows scan line 301 superimposed on cell 101 at consecutive sample times $T_1$-$T_7$. (While FIG. 3B shows the cell traversing exactly one pixel per sample time, this is not a requirement, and in fact will only occur for certain combinations of cell travel speed, sample rate, and pixel size. In practice, consecutive scanned lines may overlap on the cell being imaged, or there may be a gap between areas of the cell read by consecutive scan lines.) The light levels read by pixels a, b, c, d, and e are affected by the structure of cell 101. For example, when no cell crosses scan line 301, relatively high light levels are registered. When a relatively transparent part of cell 101 crosses a pixel, the light level registered by that pixel is somewhat reduced. When the nucleus of cell 101 is within a pixel, the light level registered at that pixel is may be significantly reduced. FIG. 3C shows traces of the light levels (on an arbitrary scale ranging from 0 to 1) registered at pixels a, b, and c as a function of time. FIG. 3D shows a reconstructed image, formed by stacking together data scanned during several consecutive line scans, and representing each numerical light reading by a printed gray level. While FIG. 3D is constructed using only a few pixels sampled at a few times and therefore shows a relatively crude depiction of cell 101, in practice a system according to an embodiment of the invention may scan more or fewer lines during the passage of each cell, and each line may contain more or fewer pixels than shown. In one embodiment the system may scan approximately 50 lines during the passage of each cell, and each line may contain approximately 50 pixels. The exact number of lines scanned and pixels affected for each cell will depend on the size of the cells, the line scan frequency, the speed at which cells flow past the scan line, and the particular sensor and optical components used.

The theoretical resolution of the system depends mainly on the quality of the objective lens. The practical sanning resolution of the system also depends on the scan rate, the speed of transport of the cells past the scan line, and the particular sensor and optical system used. The pixel resolution in the Y direction is determined by the imaging system, including the particular lens and sensor used. Pixel resolution in the X direction is equal to v·dt, where v is the sample delivery speed and dt is the camera's exposure time. Preferably, v is a known parameter, either pre-determined before a particular flow experiment or measured during the course of a cell's passage through the system. Ideally, a cell being scanned should be rotation-free and jittering-free during its passage of the scan line.

The operation of the system of FIG. 2 is described above in the context of direct light imaging, where scattered light from source 201 is measured by sensor 205. A system operating on the same principles could be used to perform fluorescence imaging as well, and in fact, the system may be especially helpful in fluorescence imaging. In that case, light from source 201 would excite fluorescence in the cell 101 being measured, and resulting emitted light would be collected and measured by sensor 205. The emitted light will generally be at a longer wavelength than the excitation light from source 201. In fluorescence imaging, it may be desirable to shield sensor 205 from receiving light from source 201, using various filters or geometric arrangements of components, so that the source light does not overwhelm or interfere with the measurement of the light emitted by fluorescence. Typically, the light emitted by fluorescence will be less intense than the source light, and longer exposure times, stronger illumination, or more sensitive sensors may be required for fluorescence imaging than for direct imaging. Also, the shape of the temporal signal changes shown in FIG. 3C may be different in fluorescent imaging than in direct imaging. In direct imaging, additional structure in a cell tends to result in less light being received by the corresponding pixel of sensor 205. In fluorescence imaging, additional structure may carry additional fluorophores, and may result in more light reaching the corresponding sensor pixel, as compared with a pixel corresponding to a cell portion with little structure.

Figure 4:
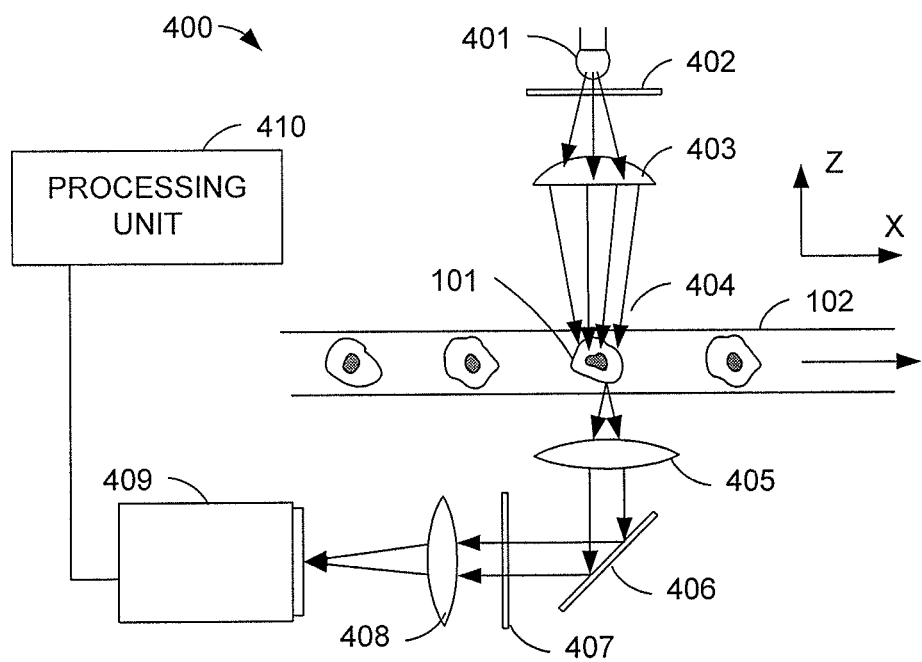
FIG. 4 shows an orthogonal view of a system in accordance with another embodiment of the invention.

FIG. 4 shows an orthogonal view of a system 400 in accordance with another embodiment of the invention. The embodiment of FIG. 4 may be especially suited to single-color fluorescence imaging cytometry. In the embodiment of FIG. 4, a light source 401 emits light. Light source 401 may be a laser, a light-emitting diode, an incandescent light source, a fluorescent light source or another kind of light source. Light source 401 may produce substantially monochromatic light, broad spectrum light, or light containing two or more narrow bands of wavelengths. In one example embodiment, light source 401 is a laser that emits light at a nominal wavelength of 488 nm. An excitation filter 402 may be utilized to further narrow the band of wavelengths of light utilized by the system, especially if light source 401 is a broad spectrum light, or otherwise produces wavelengths that are undesirable for a particular cytometry experiment. An optional light shaping element or condenser lens 403 may concentrate the emitted light at a scanning region 404, through which a cell 101 is being transported. Preferably, cell 101 has been marked with one or more fluorophores that fluoresce when excited by the light from light source 401. Many different fluorophores are known, including the ALEXA FLUOR™ series of fluorophores available from Life Technologies Corporation of Carlsbad, Calif., USA. The concentration provided by light shaping element or condenser lens 403 improves the effective illumination of cell 101, and results in a stronger fluorescent signal. The stronger signal results in less restriction on the exposure time of the sensor used in the system. The oblong or slit-shaped illumination field is well suited to light sources that have naturally asymmetric illumination patterns, for example semiconductor lasers or light emitting diodes.

Light scattered from cell 101 is gathered and redirected by objective lens 405, reflects from dichroic mirror 406, passes through tube lens 408, and reaches line scan camera 409, where sequential line images of scan region 404 are gathered for analysis by processing unit 410. An emission filter 407 may be placed in the system to narrow the band of light wavelengths delivered to camera 409. Dichroic mirror 406 may also provide filtering. This filtering may reduce the effect of direct light from source 401 that may be scattered by cell 101. Objective lens 405 and tube lens 408 preferably form an infinity-corrected optical system, such that an "infinity space" is created between them. In such a system (known in the art), the performance of the system is relatively insensitive to the distance between the objective lens and the tube lens, allowing space for the insertion of other components such as dichroic mirror 406 and emission filter 407.

Figure 5:
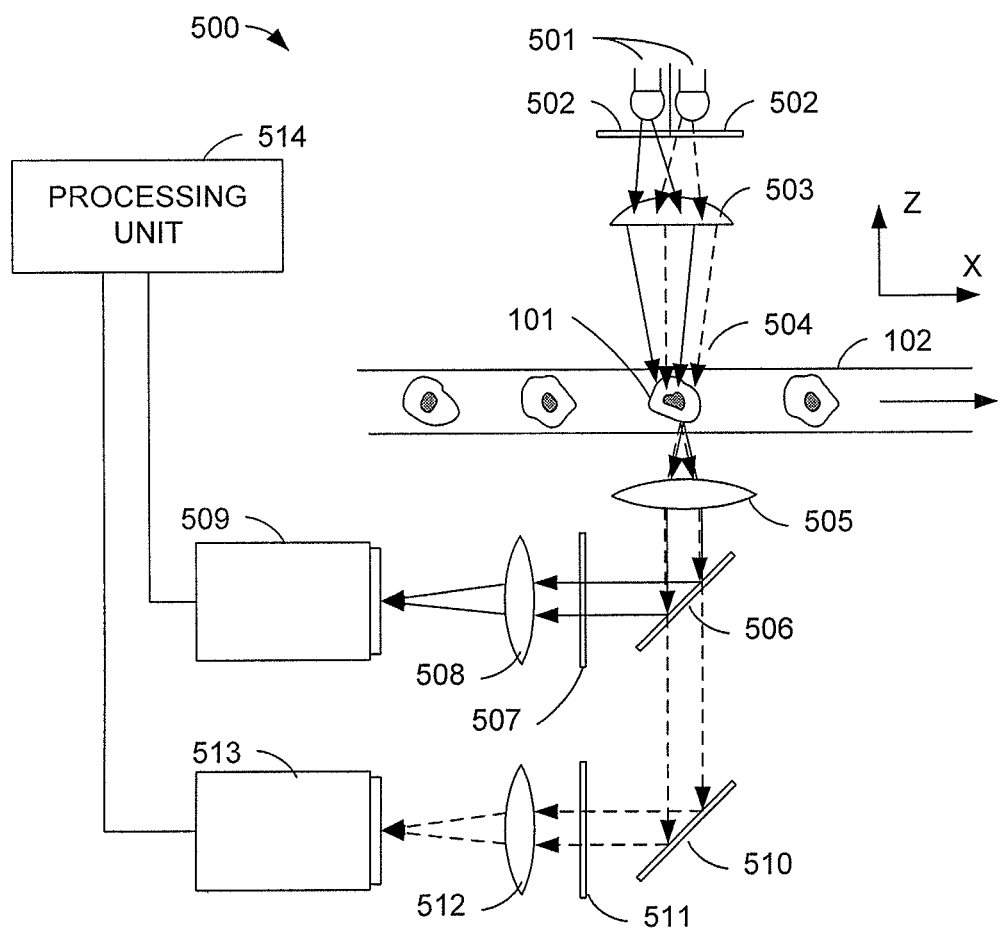
FIG. 5 illustrates an orthogonal view of a system in accordance with another embodiment of the invention.

FIG. 5 illustrates an orthogonal view of a system 500 in accordance with another embodiment of the invention. The system of FIG. 5 is configured for simultaneous two-color fluorescence imaging cytometry. In the system of FIG. 5, excitation light comprising two bands of wavelengths is provided to the cell 101 being imaged. This is represented in FIG. 5 by two light sources 501 producing light of different wavelengths indicated by the solid and dashed lines. The light may be further conditioned by one or more filters 502. Other arrangements are possible. For example, a single broad-spectrum light source may be utilized, and particular bands of wavelengths preferentially selected by filters 502. Or a single light source could be used to excite two different fluorescent wavelengths. In a preferred embodiment, light sources 501 comprise two lasers, one producing light in a first narrow band at a nominal wavelength of 532 nm and the other producing light in a second narrow band at a nominal wavelength of 633 nm. The light may be concentrated at the scan region 504 by a light shaping element or condenser lens 503. Element 503 may comprise various lenses, prisms, reflectors, or other optical components, singly or in combination, and preferably concentrates the light produced by sources 501 onto an oblong area at the scan region 504.

Preferably, cell 101 is marked with one or more fluorophores, such that when excitation light from sources 501 reaches cell 101, light of at least two different color characteristics is produced by fluorescence. For example, one fluorophore may react strongly to the 532 nm excitation light, producing emitted light with an emission peak at about 550 nm, and a second fluorophore may react strongly to the 633 nm excitation, producing emitted light with an emission peak at about 650 nm. These different emissions are approximately represented in FIG. 5 using dashed and solid lines in a way similar to the way the two colors of excitation light are represented, although it is to be understood that light represented by a particular line type after emission does not generally have the same spectral characteristics as excitation light represented by the same line type.

Light from scan region 504 is then gathered by objective lens 505, and directed to dichroic mirror 506. Mirror 506 may provide some filtering, such that light principally from a band of wavelengths is reflected from mirror 506, and the remaining light passed through. The light reflected from mirror 506 may pass through another emission filter 507 to further restrict the spectral characteristics of the light, and then pass through tube lens 508 and reach camera 509. Thus, camera 509 preferentially receives light emitted by a first fluorophore marker in cell 101, with little contamination by light from either of sources 510 or from light emitted by a second fluorophore marker. That is, the light reaching camera 509 preferably falls within a third band of wavelengths selected from the fluorescent emissions of the first fluorophore.

The light passed through dichroic mirror 506 is then reflected from another dichroic mirror 510, may pass through another dichroic emission filter 511, passes through a second tube lens 512 and to camera 513. Thus, camera 509 preferentially receives light emitted by the second fluorophore marker in cell 101, with little contamination by light from either of sources 510 or from light emitted by the first fluorophore marker. That is, the light reaching camera 513 preferably falls within a fourth band of wavelengths selected from the fluorescent emissions of the second fluorophore.

Cameras 509 and 513 then can scan simultaneous images of cell 101 in different emission spectra. The outputs of cameras 509 and 513 are passed to processing unit 514 for storage, analysis, display, or other purposes. Processing unit 514 may be, for example, a computer system or other processor-based system capable of processing the image data. Processing unit 514 may be an external stand-alone device, or integrated into a testing instrument.

Many variations are possible for the system. For example, dichroic minor 510 may be eliminated and filter 511, tube lens 512, and camera 513 positioned to directly receive the light that has passed through dichroic mirror 506. Some of the filters in the system may be optional, depending on the particular light sources and fluorescent materials used. Additional sets of light sources, filters, mirrors, lenses, or cameras may be added so that simultaneous imaging may be performed in three, four, or even more different spectral bands.

One of skill in the art will recognize that the dichroic mirrors and filters thus far described do not have perfect wavelength discrimination or perfect efficiency. Some light in the wavelength bands intended to be passed by a particular filter may be absorbed or reflected. Some light in wavelength bands intended to be blocked by a particular filter may be passed or reflected. However, the filters and mirrors perform sufficiently well to preferentially pass or block designated wavelengths that the system can discriminate different emitted light colors effectively. In other variations, components other than dichroics may be used for color separation, including prisms, gratings, or other optical components.

Figure 6:
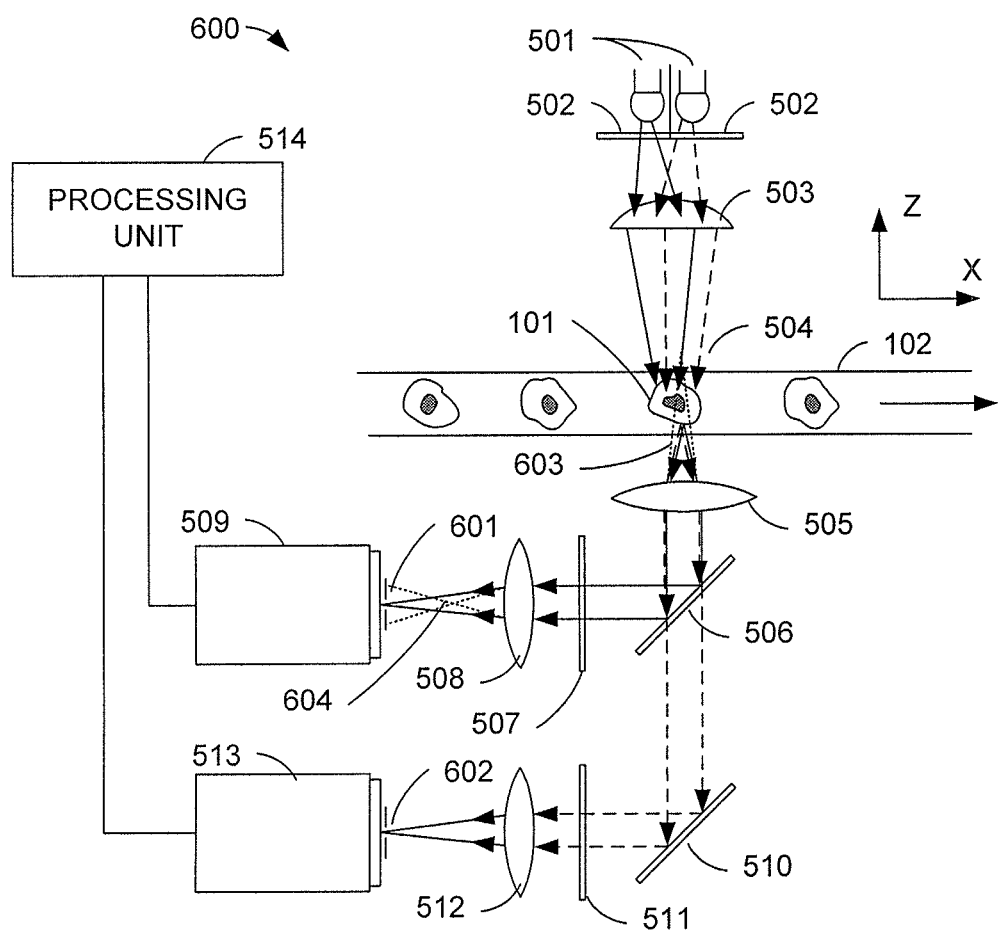
FIG. 6 illustrates an orthogonal view of a system in accordance with another embodiment of the invention.

FIG. 6 illustrates an orthogonal view of view of a system 600 in accordance with another embodiment of the invention. System 600 is similar to system 500, with the addition of slit apertures 601 and 602 placed in front of cameras 509 and 513 respectively. Slit apertures 601 and 602 have the effect of tending to block or exclude some light gathered from locations other than in the focal plane of the system from reaching the respective camera. This effect is illustrated in FIG. 6 by finely-dashed pencil of rays 603, emanating from an out-of-focus location above cell 101. The resulting pencil of rays 604 emerging from lens 508 will focus more closely to lens 508 than does the light from the focal plane of the system. By the time the light in pencil 604 reaches slit aperture 601, pencil 604 has already started to diverge, so that only a small portion of the center of pencil 604 can pass through slit 601 and reach camera 509. Thus, the system preferentially receives light from the focal plane of the system at cell 101, and excludes at least some light received from other depth locations.

When a small circular aperture is used in this way to limit the light received by a single sensor, this technique is called confocal imaging. In the system of FIG. 6, apertures 601 and 602 are slits, and therefore exclude light in only one axis. For the purposes of this disclosure, this is referred to as "semi-confocal" imaging. This technique improves the contrast of images recorded by the system as compared with images recorded by a system not utilizing semi-confocal imaging.

Another advantage of a cytometry system embodying the invention is that it may be modified or made configurable into a point-detector style system, where either only a few pixels in the middle of the linear detector are in operation or some or all the pixels in the row are binned into one pixel or a few pixels. This results in an image of reduced resolution in a dimension corresponding to the length of the linear light sensor (the Y direction in FIG. 6). Each exposure of the light sensor may even result in a single numerical representation of the amount of light falling on the sensor, for example if all of the sensor pixels are binned. Optionally, the illumination field could be shaped to a much smaller circle or ellipse, to enhance the speed of the system when operating in that mode. An advantage of this kind of system is that a very high speed single cross-section image of a cell can be generated. This kind of system may be especially useful when electronic communication bandwidth is limited, but ample illumination is available. A system configurable in this way may be applicable to both line-scan imaging cytometry, and to non-imaging flow cytometry.

Figure 7:
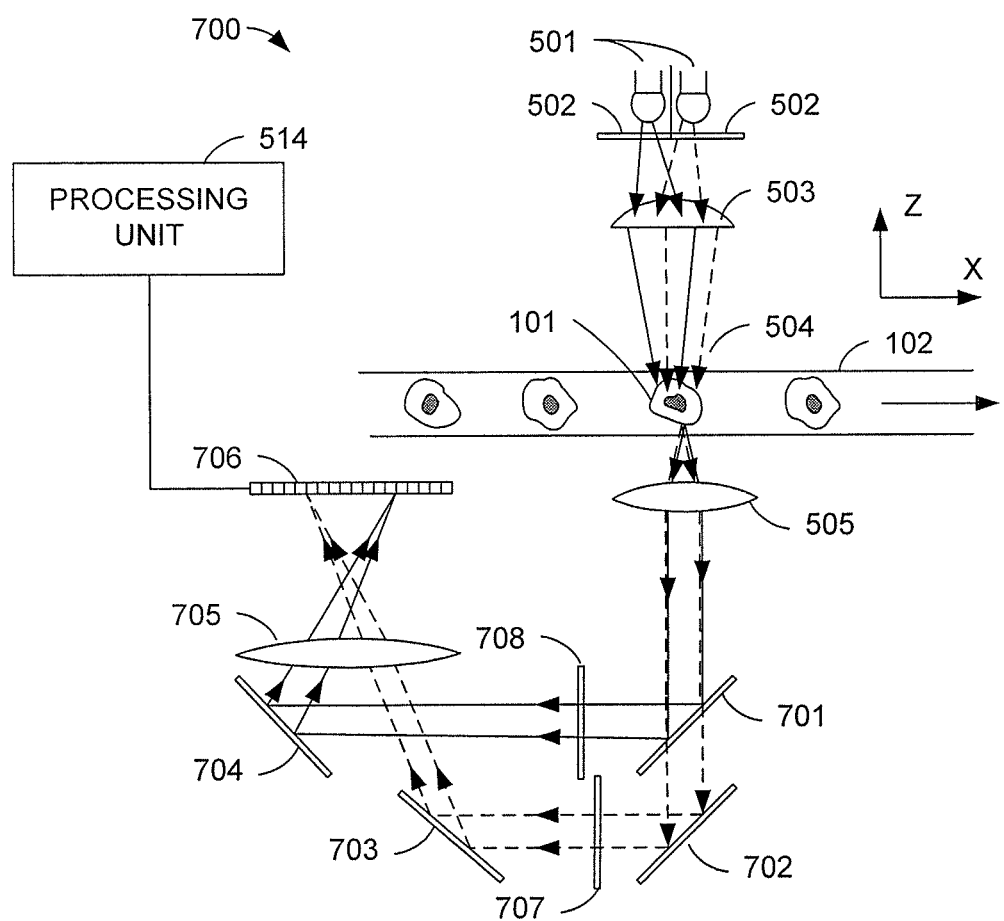
FIG. 7 illustrates an orthogonal view of a system in accordance with still another embodiment of the invention.

FIG. 7 illustrates an orthogonal view of view of a system 700 in accordance with still another embodiment of the invention. In the system of FIG. 7, simultaneous two-color fluorescence imaging cytometry is enabled using only one linear light sensor or line-scan camera. The illumination system in system 700 may be, for example, any of the illumination systems described above with respect to system 500 shown in FIG. 5. That is, one or more light sources excites two different fluorescence spectra, for example from two different fluorophores in cell 101. Some of the light emitted by fluorescence from cell 101 is captured and redirected by objective lens 505 toward dichroic mirror 701. The solid and dashed lines in FIG. 7 indicate that light containing two different fluorescence spectra reach dichroic mirror 701. Mirror 702 selectively filters the light, so that one band of wavelengths preferentially reflects from mirror 701, and other wavelengths preferentially pass through mirror 701 and continue toward mirror 702. Additional mirrors and filters may be placed in the optical system directing and conditioning the light as desired. For example, mirror 703 redirects the light from mirror 702 toward tube lens 705, and mirror 703 may also provide additional filtering. Similarly, mirror 704 redirects the light from mirror 701 toward tube lens 705, and mirror 704 may also provide filtering. One or more additional filters such as emission filters 707 and 708 may be placed in the optical path. Tube lens 705 refocuses the light onto linear light sensor 706, which may be part of a line scan camera, and can be read by processing unit 514.

The arrangement of mirrors provides a geometric offset between the two bands of light reaching sensor 706, so that part of sensor 706 receives light in one wavelength band, selected from the light emitted in one of the fluorescence spectra, and another part of sensor 706 receives light in the other wavelength band, selected from light emitted in the other fluorescence spectrum. For example, if sensor 706 comprises 512 pixels arranged in a row, then approximately the first 256 pixels may receive light in one band of wavelengths, while, approximately the remaining 256 pixels may receive light in the other wavelength band. As above, processing unit 514 receives repeated line scans from sensor 706, and can reconstruct two images of cell 101, one image for each wavelength band. Such a system requires only one linear light sensor or line scan camera, and may be constructed at reduced cost as compared with a system having two linear light sensors or line scan cameras. Other kinds of optical systems may also be used to direct light in two wavelength bands to separate portions of a linear light sensor. For example, such an optical system may comprise an optical grating. A slit aperture may be included in a system such as system 700, so that the system performs semi-confocal imaging.

Figure 8:
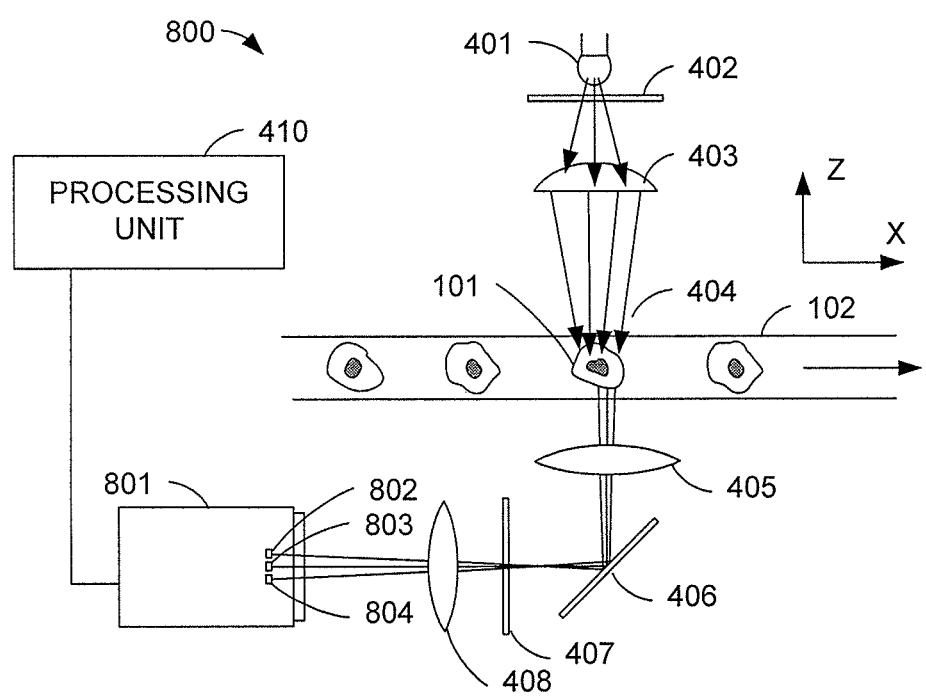
FIG. 8 illustrates an orthogonal view of a system in accordance with another embodiment.

FIG. 8 illustrates an orthogonal view of view of a system 800 in accordance with still another embodiment. System 800 is illustrated as a variant of system 400, shown in FIG. 4, but one of skill in the art will recognize that the additional features of system 800 may be employed in other systems, including ones that perform multi-color imaging, fluorescence imaging, or other techniques.

System 800 employs an exemplary camera 801 having three closely spaced parallel rows of sensors 802, 803, 804. (The sensor rows are shown end-on in FIG. 8.) By virtue of the operation of the optics of the system, each of the rows images a different "stripe" on cell 101. Camera 801 thus has three different opportunities to image any particular part of cell 101 as cell 101 passes by the scanning region 404. That is, a particular part of cell 101 will be imaged onto row 802 at a first time. That same part of cell 101 will be imaged onto row 803 at a later time, and onto row 804 at a still later time. In FIG. 8, only the central rays of pencils connecting cell 101 with sensor rows 802, 803, 804 are shown, so as not to obscure the operation of the system in unnecessary detail.

In one technique, three different images may be gathered of cell 101, one made by each of sensor rows 802, 803, 804. The different images are shifted in time with respect to each other, or may also be thought of as shifted in space, in the X direction. These multiple images may be used to create a composite image with improved signal-to-noise characteristics. For example, if the three images are digitally shifted back into alignment and pixel values from the three images corresponding to substantially the same locations on cell 101 added, the resulting composite image will have a signal-to-noise ratio improved by a factor of approximately $\sqrt{3}$ as compared with any one of the individual images. While camera 801 has been illustrated as having three scan lines, it may have 2, 4, or any usable number n. A composite image produced by this digital addition or averaging technique from a camera having n lines will have a signal-to-noise ratio improved by a factor of approximately $\sqrt{n}$ as compared with a single image. The combination of the images may be done "on the fly" as the scanned image lines are available, so that no complete image of a particular cell made by a single linear sensor is constructed.

Camera 801, having multiple rows of pixels, may additionally or alternatively be configured to perform time delay integration (TDI). In TDI, the electrical charges in the various pixels resulting from an exposure to cell 101 are accumulated within the pixel rows before conversion to digital values. The exposures of the sensors to cell 101 are substantially synchronized such that a particular location on cell 101 is exposed to sensor row 802 during one exposure, to sensor row 803 during the next exposure, and to sensor row 804 during the next exposure. Charges accumulated in row 802 during the first exposure are shifted into row 803 and added to by the second exposure, and the resulting charges are shifted into row 804 and added to by the third exposure. The accumulated charges are then converted to digital values. TDI also results in an approximately $\sqrt{n}$ improvement in signal-to-noise ratio as compared with a single image.

One advantage of scanning simultaneous parallel image lines, whether for use with digital image combination or TDI, is that the technique takes better advantage of the available illumination. A light shaping element such as element 403 will not generally focus light onto a single-pixel-wide strip at the scan line. The illumination field will have some appreciable width, and some of the illumination may be wasted in a single-line camera system.

Another advantage of such a system is that the resolution is not compromised, as it may be in systems that simply bin pixels in order to improve signal-to-noise characteristics.

One of skill in the art will recognize that a system such as system 500 shown in FIG. 5 could also be adapted such that each camera 509, 513 includes a set of two or more linear light sensors. Imaging would be performed by each camera 509, 513 as described above with respect to camera 801, so that multi-color imaging may be accomplished by digital image combination or TDI.

Similarly, a system such as system 700 shown in FIG. 7 could be adapted so that sensor 706 is replaced by a set of at least two linear light sensors. The system would then direct wavelength-selected light separately to two portions of the set of linear light sensors.

The systems of FIGS. 2, 4, 5, 6, and 7 may be thought of as including a "set" having a single linear light sensor.

Additionally, combining images from at least two parallel linear light sensors, whether by digital combination or by time delay integration, can be combined with binning or other resolution-reducing techniques. Binning may produce an image with further improved signal-to-noise characteristics, albeit at a reduced resolution.

Figure 9A:
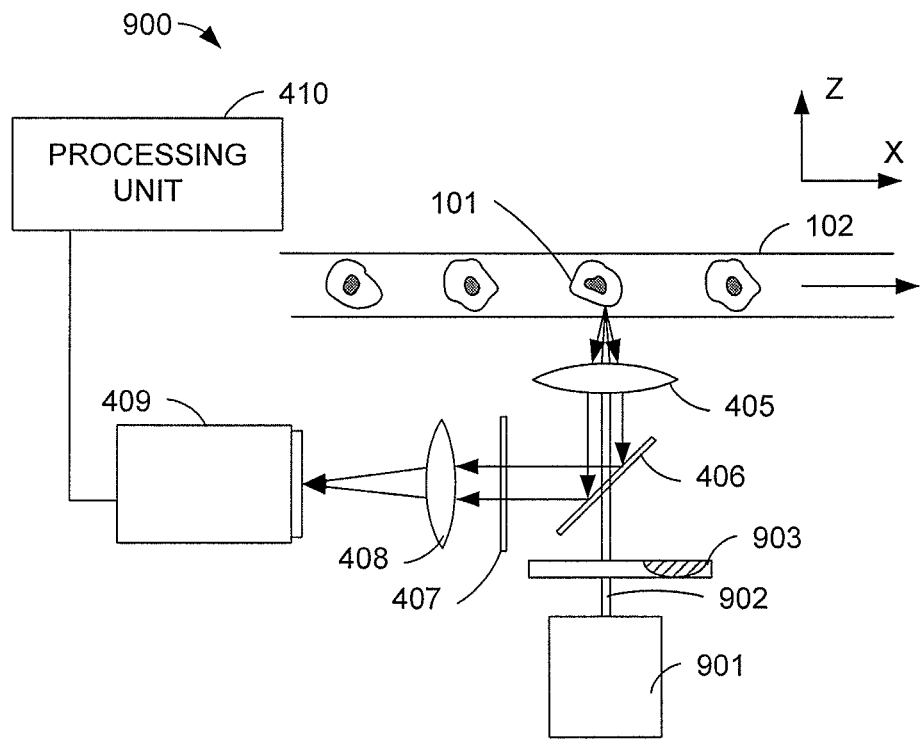
FIGS. 9A-9C illustrate embodiments of a system for producing an oblong illumination field.
Figures 9B, 9C:
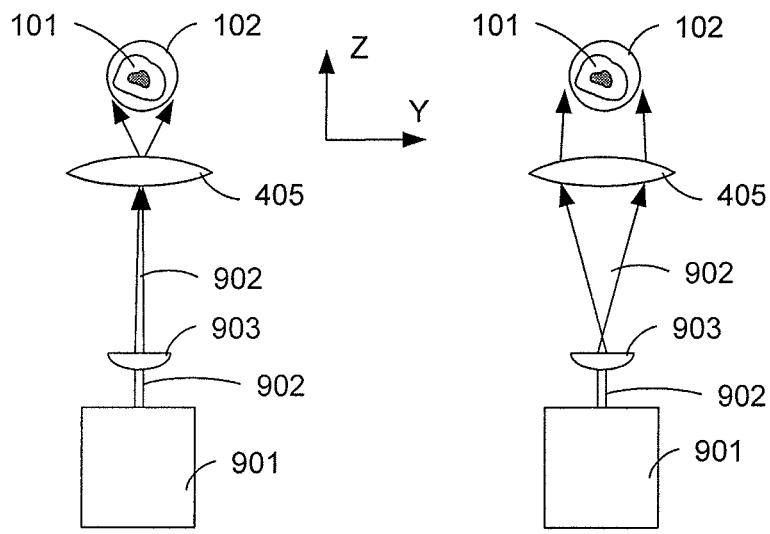

FIGS. 9A-9C illustrate additional techniques for providing an oblong illumination field convenient for performing line-scan cytometry.

The line-scan cytometry technique may not require the use of an oblong illumination field in all embodiments. Conventional circular epi-illumination may be utilized, providing the illumination power is sufficiently high. For imaging using scattered, non-fluorescent light, sufficient power of the illumination source may not be difficult to achieve. However, for practical sensing of light emitted by fluorescence, concentrating the excitation light into an oblong field can be much more energy-efficient, for example reducing the required excitation laser power from a level measured in tens or hundreds of watts to a level measured in tens or hundreds of milliwatts.

FIG. 9A illustrates one view of a system 900 that includes an embodiment of a technique for providing an oblong illumination field. System 900 uses some components and arrangements similar to those of system 400 shown in FIG. 4, but one of skill in the art will recognize that the illumination technique illustrated in FIG. 9A may be used with other sensing arrangements as well. In system 900, illumination is provided by a laser 901 from the same direction as from which sensing is performed, so that the space above the sample is left unobstructed. This arrangement may therefore accommodate much larger samples that the arrangements previously described, which may be limited to samples no thicker than the distance between the sample stage and the condenser lens. Another advantage of the system of FIG. 9A is that objective lens 405 participates in the formation of the illumination field. Objective lens 405 may typically be a very high-quality lens, so that the illumination field it produces may be very sharply defined.

In the example system of FIG. 9A, laser 901 produces a beam 902, directed at cell 101. Beam 902 passes through a cylindrical lens 903. For the purposes of this disclosure, a cylindrical lens is any lens that has curvature in only one dimension. A cylindrical lens may but need not have curved surfaces defined by circular cylinders. In the view of FIG. 9A, cylindrical lens 903 is positioned with its cylindrical axis parallel to the X direction, and lens 903 appears to have no effect on beam 902. Beam 902 continues through dichroic mirror 406 to objective lens 405, which focuses the beam onto cell 101. Light emanated from cell 101 passes through objective lens 405, preferentially reflects from mirror 406, may encounter one or more filters 407, passes through lens 408, and reaches camera 409.

FIG. 9B illustrates an embodiment of the illumination portion of FIG. 9A, from a view along the X axis. That is, FIG. 9B shows a view rotated 90 degrees from the view of FIG. 9A. In this view, tube 102 projects as a circle, and cylindrical lens 903 shows as having a curved profile. In the example embodiment of FIG. 9B, the materials and dimensions of cylindrical lens 903 are selected such that lens 903 has a relatively long focal length—greater than the distance between the cylindrical lens and the objective lens. After passing through cylindrical lens 903, beam 902 is seen to relatively gradually converge, as seen in this view. Objective lens 405 then converges and reexpands the beam in the Y direction, such that the illumination field is widened. As is shown in FIG. 9A, objective lens 405 simultaneously focuses the beam in the X direction. The resulting illumination field may have a sharply-defined oblong shape as it encounters cell 101.

FIG. 9C illustrates another embodiment of the illumination portion of FIG. 9A, from a view along the X axis. In this embodiment, the materials and dimensions of cylindrical lens 903 are selected such that lens 903 has a relatively short focal length—shorter than the distance between the cylindrical lens and the objective lens. After passing through cylindrical lens 903, beam 902 is seen to converge and then rediverge before reaching objective lens 405. Objective lens 405 redirects beam 902 such that it again converges, but slowly enough that when beam 902 reaches cell 101, beam 902 is still sufficiently wide to span at least a portion of the line being scanned by camera 409. Again, objective lens 405 simultaneously focuses the beam in the X direction. The resulting illumination field may have a sharply-defined oblong shape as it encounters cell 101.

While embodiments of the invention have been illustrated as scanning cells confined in a linear tube, one of skill in the art will recognize that embodiments of the invention may be utilized in systems using any of a wide range of cell delivery techniques, including electrophoresis, pressure driven flow, optical tweezers, motorized translation stage, and others. Cells may be conveyed as a payload in an oil emulsion, in an electrowetting-actuated droplet, or via magnetic transport assisted by magnetic bead tagging. It is intended that the claims not be limited by the cell delivery method utilized.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. The invention has now been described in detail for the purposes of clarity and understanding. However, those skilled in the art will appreciate that certain changes and modifications may be practiced within the scope of the appended claims.

What is claimed is:

1. A system for performing cytometry, the system comprising:
   a light source that illuminates a scanning region;
   at least two parallel linear light sensors; and
   an optical system that focuses an image of a portion of the scanning region onto the at least two parallel linear light sensors;
   wherein the system repeatedly takes readings of light falling on the linear sensors while a cell is transported through the scanning region and illuminated by the light source.

2. The system of claim 1, further comprising a slit aperture proximate the linear sensors, such that the system performs semi-confocal imaging.

3. The system of claim 1, wherein images gathered by the individual linear light sensors are combined to form an image with improved signal-to-noise characteristics as compared with an image gathered by a single linear light sensor.

4. The system of claim 3, wherein the images are combined by digitally combining pixel values from the respective images corresponding to substantially the same respective locations on the cell.

5. The system of claim 3, wherein the images are combined by time delay integration.

6. The system of claim 1, further comprising a light shaping element that concentrates light from the light source onto an oblong field at the scanning region.

7. A system for performing cytometry, the system comprising:
   a scanning region that is illuminated by light including at least first and second wavelength bands;
   means for transporting a cell through the scanning region such that the cell is illuminated;
   first and second sets of linear light sensors, each set comprising at least one linear light sensor; and
   an optical system that selectively directs light emitted from the cell to the two linear light sensor sets such that emitted light in a third wavelength band is primarily directed to the first linear light sensor set, and emitted light in a fourth wavelength band is primarily directed to the second linear light sensor set;
   wherein the system repeatedly takes readings of light falling on the linear sensors while the cell is transported through the scanning region.

8. The system of claim 7, wherein each linear light sensor set comprises at least two linear light sensors.

9. The system of claim 7, wherein the emitted light is emitted as a result of fluorescence.

10. The system of claim 7, wherein the optical system further comprises:
    an objective lens that receives and redirects light emitted from the cell;
    a mirror that reflects a first portion of the redirected light to the first linear light sensor set and transmits a second portion of the redirected light.

11. The system of claim 10, further comprising:
    a first tube lens that receives the first portion of light and cooperates with the objective lens to form an image of the cell on the first linear light sensor set.

12. The system of claim 11, further comprising a second tube lens that receives the second portion of light and cooperates with the objective lens to form an image of the cell on the second set of linear light sensors.

13. The system of claim 7, further comprising a slit aperture proximate at least one of the sets of linear light sensors, such that the system performs semi-confocal imaging.

14. The system of claim 7, wherein each set of linear light sensors comprises at least two linear light sensors, and wherein for each set of linear light sensors, images gathered by the individual linear light sensors in the set are combined to form an image with improved signal-to-noise characteristics as compared with an image gathered by a single linear light sensor in the set.

15. The system of claim 14, wherein the images are combined by digitally combining pixel values from the respective images corresponding to substantially the same respective locations on the cell.

16. The system of claim 14, wherein the images are combined by time delay integration.

17. A system for performing cytometry, the system comprising:
    a scanning region that is illuminated by a light source;
    a set comprising at least two linear light sensors; and
    an optical system that focuses an image of a portion of the scanning region onto the linear light sensor set;
    wherein the system repeatedly takes readings of light falling on the linear light sensor set while a cell is transported through the scanning region and illuminated by the light source;
    and wherein the system is configurable such that during a first experiment, a first image is created having a first number of pixels in a dimension corresponding to the length of the linear light sensor set, and during a second experiment, a second image is created having a second number of pixels in the dimension corresponding the length of the linear light sensor set, the second number of pixels being fewer than the first.

18. The system of claim 17, wherein the system is configured such that the number of pixels in the second image is reduced by selecting fewer than all of the pixels from the linear light sensor set.

19. The system of claim 17, wherein the system is configured such that the number of pixels the second image is reduced by binning some or all of the pixels from the linear light sensor set.

20. The system of claim 17, wherein the system is configured such that each reading of light falling on a particular linear sensor results in a single numerical representation of the amount of light falling on the particular sensor.

21. A method of performing cytometry, the method comprising:
    illuminating, using a light source, a scanning region;
    focusing, using an optical system, an image of a portion of the scanning region onto at least two parallel linear light sensors;
    repeatedly taking readings of light falling on the two parallel light sensors while a cell is transported through the scanning region and illuminated by the light source.

22. The method of claim 21, further comprising combining images gathered by the individual linear light sensors to form an image with improved signal-to-noise characteristics as compared with an image gathered by a single linear light sensor.

23. The method of claim 22, wherein combining images further comprises digitally combining pixel values from the respective images corresponding to substantially the same respective locations on the cell.

24. The method of claim 22, wherein combining images further comprises combining images using time delay integration.

25. The method of claim 21, wherein the light source produces illumination including light in at least first and second wavelength bands, and wherein the method further comprises:

directing, using the optical system, light emitted from the cell in a third wavelength band primarily to one of the two parallel light sensors, and directing, using the optical system, light emitted from the cell in a fourth wavelength band primarily to the other of the two parallel linear light sensors.

26. The method of claim 21, further comprising focusing, using the optical system, an image of a portion of the scanning region onto at least two sets of parallel linear light sensors, each set comprising at least two linear light sensors.

\* \* \* \* \*